(12) United States Patent
Dee et al.

(10) Patent No.: US 8,043,626 B2
(45) Date of Patent: *Oct. 25, 2011

(54) FATTY ACID ANTIMICROBIAL

(75) Inventors: Alejandro O. Dee, San Ramon, CA (US); Charles D. Gradle, Oak Park, IL (US)

(73) Assignee: GEA Farm Technologies, Inc., Naperville, IL (US)

( * ) Notice: Subject to any disclaimer, the term of this patent is extended or adjusted under 35 U.S.C. 154(b) by 165 days.

This patent is subject to a terminal disclaimer.

(21) Appl. No.: 12/322,437

(22) Filed: Feb. 2, 2009

(65) Prior Publication Data

US 2009/0275657 A1   Nov. 5, 2009

Related U.S. Application Data

(63) Continuation of application No. 10/786,209, filed on Feb. 25, 2004, now Pat. No. 7,553,871, and a continuation of application No. 08/602,498, filed on Feb. 20, 1996, now Pat. No. 6,699,907.

(51) Int. Cl.
*A01N 25/04* (2006.01)

(52) U.S. Cl. ........ 424/405; 424/438; 514/558; 514/559; 514/560

(58) Field of Classification Search .......... 514/558, 514/559; 424/405, 438
See application file for complete search history.

(56) References Cited

U.S. PATENT DOCUMENTS

| | | | |
|---|---|---|---|
| 4,404,040 A | 9/1983 | Wang | |
| 4,406,884 A | 9/1983 | Fawzi et al. | |
| 4,485,029 A | 11/1984 | Kato et al. | |
| 5,208,257 A | 5/1993 | Kabara | |
| 5,436,008 A | 7/1995 | Richter et al. | |
| 5,460,833 A | 10/1995 | Andrews et al. | |

FOREIGN PATENT DOCUMENTS

| | | |
|---|---|---|
| CA | 553057 | 2/1958 |
| DE | 29 12 438 | 10/1980 |

OTHER PUBLICATIONS

English language Translated Description and Claims of DE 29 12 438, European Patent Office's esp@cenet.com database, 3pp, 1980.

Dunham et al., Inactivation of Influenza Virus by Mild Antiseptics, pp. 123-128 (1943).
Barr et al., A Study of the Inhibitory Concentrations of Glycerin-Sorbitol and Propylene Glycol-Sorbitol . . . ,Jnl. of the Am. Pharm. Assoc., vol. 46, No. 4, pp. 217-218 (1956).
Olitzky, Antimicrobial Properties of a Propylene Glycol Based Topical Therapeutic Agent, vol. 54, No. 5, pp. 787-788 (1965).
Kabara et al., Fatty Acids and Derivatives as Antimicrobial Agents, Antimicrobial Agents and Chemotherapy, vol. 2, No. 1, pp. 23-28 (1972).
Freese et al., Function of Lipophilic Acids as Antimicrobial Food Additives, Nature, vol. 241, pp. 321-325 (1973).
Fay et al., Inhibitory Action of a Non-Metabolizable Fatty Acid on the Growth of *Escherichia coli*: Role of . . . , Journal of Bacteriology, vol. 132, pp. 790-795 (1977).
Kabara et al., Antimicrobial Lipids: Natural and Synthetic Fatty Acids and Monoglycerides, Lipids, vol. 12, No. 9, pp. 753-759 (1977).
Heczko et al., Susceptibility of *Staphylcoccus aureus* and Group A, B, C, and G Streptococci . . . , Jnl. of Clinical Microbiology, vol. 9, No. 3., pp. 333-335 (1979).
Kabara, Toxicological, Bacteriocidal and Fungicidal Properties of Fatty Acids and Some Derivatives, J. Am. Oil Chemists' Soc., vol. 56, pp. 760A-767A (1979).
Thomas et al., Antibacterial Properties of Dilute Formocresol and Eugenol and Propylene Glycol, Oral Surgery, vol. 49, No. 2, pp. 166-170 (1980).
Corner, Synergism in the Inhibition of *Bacillus subtilis* by Combinations . . . , Antimicrobial Agents and Chemotherapy, vol. 19, No. 6, pp. 1082-1085 (1981).
Pankey et al., Uptake on Postmilking Teat Antisepsis, J. Dairy Sci., vol. 67, No. 6, pp. 1336-1353 (1984).
Bolton et al., Repair and Antibacterial Effects of Topical Antiseptic Agents in vivo, Models in Dermatology, vol. 2, pp. 145-158 (1985).
Viegas et al., Inhibition of Yeast Growth by Octanoic and Decanoic Acids . . . , Appl. and Environmental Microbiology, vol. 55, No. 1, pp. 21-27 (1989).
3M Lauricare Moisturizing Teat Dip Concentrate, Test Data & Results, 2 pp, date unknown.

*Primary Examiner* — Neil Levy
(74) *Attorney, Agent, or Firm* — Smith Law Office

(57) ABSTRACT

The novel antimicrobial composition is disclosed including from about 60 to 95% of a lipophilic polar solvent such as propylene glycol, ethylene glycol, or isopropanol and from about 0.5 to 5% of a mixture of $C_8$ to $C_{14}$ fatty acids. Other constituents of the present invention may include water, an alcohol (such as ethanol or propanol) or a mixture thereof. Also disclosed is a novel method of killing harmful microbes on the udder of a milk-producing animal using the above-mentioned composition.

24 Claims, No Drawings

FATTY ACID ANTIMICROBIAL

This application is a continuation of application Ser. No. 10/786,209 filed Feb. 25, 2004 now U.S. Pat. No. 7,553,871 and application Ser. No. 08/602,498 filed Feb. 20, 1996, now U.S. Pat. No. 6,699,907, the disclosures of which are incorporated by reference herein.

FIELD AND BACKGROUND OF THE INVENTION

This invention is directed to an antimicrobial composition, and in particular to an antimicrobial composition including a mixture of fatty acids of differing lengths and a lipophilic polar solvent.

BACKGROUND OF THE INVENTION

The treatment and prevention of mastitis in dairy cows continues to be of primary importance to those engaged in the dairy farming industry. The combined costs of mastitis to the U.S. dairy farming industry have been estimated at between two and three billion dollars annually.

Mastitis is caused by infections of the mammary, or milk-producing, glands by a broad spectrum of pathongenic microorganisims such as *Staphylococcus aureus, Streptococcus agalactiae, Escherichia coli, Mycoplasma bovis* and *Candida albicans*. In particular, when the milk-producing glands and surrounding tissues in the udder become infected, the tissues become inflamed with cellular infiltrates and associated toxic substances.

The cellular infiltrates and associated toxins, along with the infecting organisms themselves, can cause a dramatic reduction in the quality of milk produced by the animal. The infiltrates, toxins, and organisms can also affect the quantity of milk produced by the animal, possibly even resulting in the stoppage of production.

Occasionally, the infection can spread systemically to other organ and tissue sites via the blood or lymphatic systems. The spreading infection can, in extreme cases, seriously debilitate or kill the infected animal.

Given the importance of the mastitis problem to dairy farmers, several methods have been proposed to combat this menace. One method frequently used to combat the problem has been to "cull" out or separate the infected animals from the herd, and then to treat the infected animals with antibiotics. Antibiotics can be administered either directly (via an injection) or indirectly (via feed).

The secondary problem of antibiotic residues in the treated animal and their milk products, however, has come under increased scrutiny from federal and state regulatory agencies, such as the United States Department of Agriculture and the Food and Drug Administration. Additionally, public outcry over the use of antibiotics and the presence of antibiotics residues in meat and milk products has severely limited the market for such products.

As an alternative to treatment with antibiotics after infection, products have been designed to prevent mastitis by killing the pathogenic organisms which might otherwise infect the teat and udder tissues before the organisms enter the tissues. One such proactive product is a topical antiseptic commonly known as teat (or udder) dip, wash, spray, or wipe. This product is applied to the teat and udder area of the dairy cow or other milk-producing animal before and/or after milking as part of a process of general dairy hygiene. The product is intended to kill or reduce in number the mastitis-causing microorganisms on the surface of the teat before the microorganisms have had a chance to migrate or be propelled (during milking) into the teat canal, or to enter the teat via injuries or lesions.

Although the wide-spread use of topical antiseptics in the last 30 years has greatly decreased the incidence of mastitis, many of the products presently in use as teat dips, washes, sprays or wipes (broad-spectrum chemical germicides such as chlorinated compounds, iodophors or chlorhexidines) are known to irritate the animals' skin. This is particularly significant because the cow is subjected to repeated applications of the product, two or three times a day, before and/or after milking, for a period of years. In some cases, these germicides have actually been found to be toxic to the animals and to the human dairy workers.

Additionally, there is growing concern among the federal and state regulatory agencies, such as the Food and Drug Administration, about the presence of germicide residues, such as iodine or chlorhexidine, in milk products.

Furthermore, chemical germicides such as chlorine, iodine and chlorhexidine compounds lack a high degree of stability. These chemical germicides can be become inactivated over time, or can become inactivated by substances (such as water or organic materials) which may contaminate or dilute the germicide after it has been applied to the teat.

The lack of stability is a particularly significant disadvantage considering that, in some applications, teat dips, washes, sprays, and wipes are intended to remain on the teat and udder for hours at a time so as to provide extended protection from pathogenic microbes between milkings. In fact, for compounds such as chlorine dioxide, the lack of stability over time becomes even more significant in that the time between the preparation of the product by the farmer and the application of the product to the animal may be at least two or three hours. The lack of stability over time also negatively impacts the ability of the dairy farmer to store, for example, compositions made of chloride dioxide for use at a later date.

One suggested substitute for the chlorinated compounds, iodophors, and chlorhexidines presently used as teat dips are the fatty acids and their derivatives. The antimicrobial or germicidal properties of short to medium-chain fatty acids ($C_6$ to $C_{14}$) and their derivatives (such as esters) have been widely known for some time. See U.S. Pat. No. 4,406,884; Fawzi and U.S. Pat. No. 5,208,257 to Kabara; Viegas, et al., Inhibition of Yeast Growth by Octanoic and Decanoic Acids Produced during Ethanolic Fermentation, Applied and Environmental Microbiology, January 1989; J. J. Kabara, Toxicological, Bactericidal and Fungicidal Properties of Fatty Acids and Some Derivatives, Journal of American Oil Chemists' Society, November 1979; J. Fay and R. Farias, Inhibitory Action of a Non-Metabolizable Fatty Acid on the Growth of *Escherichia coli*: Role of Metabolism and Outer Membrane Integrity, Journal of Bacteriology, December 1977; and J. J. Kabara, Antimicrobial Lipids: Natural and Synthetic Fatty Acids and Monoglycerides, Lipids, March 1977. Fatty acids have been included in the class of lipophilic weak acids which are generally considered to be an important class of antimicrobial agents. See Thomas R. Corner, Synergism in the Inhibition of *Bacillus* subtilin by Combinations of Lipophilic Weak Acids and Fatty Alcohols, Journal of Antimicrobial Agents and Chemotherapy, pp. 1082-85 (June 1981).

While highly bactericidal, undiluted fatty acids are irritating to the skin, and may even be corrosive. Fortunately, it has been found that dilute concentrations of fatty acids have antimicrobial efficacy. Hence, a significant amount of work has been done to prepare antimicrobial compositions using a fatty-acid diluted, for example, with water.

Preparing such a composition diluted with water is complicated because short to medium-chain fatty acids are, at best, only slightly soluble in water. One solution to the relative insolubility of fatty acids has been to add hydrotropes to compositions containing low concentrations (0.1 to 5.0% by weight) of a mixture of fatty acids ($C_6$ to $C_{12}$) to solubilize the fatty acids. In such a composition, the shorter-chained fatty acids ($C_6$ to $C_9$) may actually assist the action of the hydrotrope by helping to solubilize the longer species, and thereby improving the longer species' antimicrobial efficacy. See U.S. Pat. No. 4,404,040 to Wang et al.

To maintain the antimicrobial action of the fatty acids in solution with water, however, the pH of the composition must be sufficiently low (below 4.0) to allow the acids to remain in their active free acid form. A strong organic or inorganic acid must be added to lower the pH so that the fatty acid can remain in its active form.

Alternatively, while teaching a fatty acid composition diluted with water, U.S. Pat. No. 4,406,884 to Fawzi et al. teaches away from solubilizing the fatty acids in water. Instead, Fawzi teaches that the antimicrobial efficacy of the fatty acids may be enhanced by supersaturating the aqueous phase of an aqueous lotion or gel with low concentrations of a mixture of short and medium-chain fatty acids. According to Fawzi, the supersaturated aqueous phase combined with the lipophilicity of the fatty acids provides the increased antimicrobial action, without resort to either a hydrotrope or solubilizer to maintain the fatty acids in solution with the water.

Fatty acids have been found to be more soluble in vehicles other than water. In fact, while not specifically suggested as an antimicrobial, it has been disclosed that high concentrations (5% by weight or more) of a single length of fatty acid ($C_{10}$, for example) in solution with ethanol or propylene glycol may have some efficacy in the treatment of skin diseases, such as erythroquamose and papulose. See German Laid-Open Application No. 2,912,438 to Eckert et al.

SUMMARY OF THE INVENTION

A novel antimicrobial composition is disclosed including from about 60 to 95% of a lipophilic polar solvent, such as propylene glycol, ethylene glycol, glycerol, or isopropanol, and from about 0.5 to 5% of a mixture of $C_8$ to $C_{14}$ fatty acids. Other constituents of the present invention may include water, an alcohol (such as ethanol or propanol) or a mixture thereof.

Also disclosed is a novel method of killing harmful microbes on the udder of milk-producing animal using the above-mentioned composition.

Accordingly, it is an object of the present invention to provide an effective antimicrobial potent enough to kill a broad-spectrum of harmful microorganisms.

It is another object of the invention to provide an effective antimicrobial which is non-irritating upon application.

It is a further object of the invention to provide an effective antimicrobial that is non-toxic to animals and to humans working with the animals.

It is an additional object of the invention to provide an effective antimicrobial that does not pose a significant health-risk as a residual in the milk produced by the animals to which it is applied.

It is still another object of the invention to provide an effective antimicrobial that is stable over time and with variations in concentration/contaminants, and provides an enhanced residual effect when applied to a teat or udder.

DISCLOSURE OF THE PREFERRED EMBODIMENTS

The preferred embodiment of the present invention is a solution of 70% by weight to propylene glycol as the primary solvent and 1.0% by weight of a mixture of $C_8$ and $C_{10}$ aliphatic fatty acids as the solute. The fatty acid mixture preferably includes 55% by weight $C_8$ fatty acid and 40% by weight $C_{10}$ fatty acids, with the remaining 5% by weight of the fatty acids mixture being made up of other short to medium-chain fatty acids. The remaining 29% by weight of the composition includes water as a secondary solvent, with trace concentrations of compatible perfumes and dyes. Additionally, a preservative such as methyl paraben or propyl paraben may be added to increase the life of the composition. These constituents are combined to form a solution using methods known to one of ordinary skill in the art.

The present invention is not limited to the composition of the preferred embodiment, but may contain a variety of primary and secondary solvents and solutes in accordance with the teachings of this disclosure. The concentrations of solvents and solutes may also be varied while remaining within the scope of the present invention.

For example, the primary solvent may be selected from the group of lipophilic polar solvents including propylene glycol, ethylen glycol, glycol, and isopropanol. The secondary solvent may include water, an alcohol (such as ethanol or propanol) or a mixture thereof.

Preferably, the mixture of fatty acids is a combination of $C_8$ and $C_{10}$ aliphatic fatty acids. However, mixtures of short to medium-chain aliphatic fatty acids, such as $C_8$, $C_{10}$, $C_{12}$ and $C_{14}$ aliphatic fatty acids, are encompassed by the present invention.

Additionally, the concentration of the primary solvent may vary from about 60 to 95% by weight of the composition. The concentration of the solute may also vary from about 0.5 to 5% of the composition, and the $C_8$ and $C_{10}$ fatty acids in the solute may also vary about the preferred concentrations of 55% and 40%, respectively.

Formulations of the preferred embodiments have demonstrated impressive antimicrobial efficacy against a broad spectrum of mastitis-causing microorganisms, both in vitro in the laboratory and in vivo during testing with dairy cows. The formulations of the preferred embodiments have been shown to have germicidal efficacy comparable to such popular chemical germicides as the iodophors, chlorhexidine-based compounds and chlorine-based compounds. Additionally, the mixture of fatty acids with a lipophilic polar solvent as disclosed has been shown to be superior in action to compositions wherein a lipophilic polar solvent and a single length fatty acid is used.

EXAMPLE 1

A set of in vitro tests was run on *Staphylococcus aureus, Escherichia coli, Streptococcus agalactiae, Streptococcus uberis, Staphylococcus epidermidis,* and *Pseudomonas aeruginosa*. A culture of the microorganism was first prepared according to the following procedure. Six to ten milliliters of trypticase soy broth was inoculated with the organism under consideration from a frozen or refrigerated stock. After incubation for five to seven hours at 37° C., the culture was transferred to a flask containing trypticase soy broth. The culture in the flask was then incubated on a gyratory shaker at approximately 1500 rpm overnight at 37° C. The next day, the culture in the flask is washed once in phosphate buffered saline solution (PBS) and stored at approximately 4° C. until needed.

To test a specific antimicrobial's efficacy, ten milliliters of the culture was transferred to a 15 milliliter centrifuge tube and centrifuged at approximately 600 to 700 g for approximately five to ten minutes. After decanting the supernatant, ten milliliters of the antimicrobial (or PBS in the negative, or untreated, control) was added, and the centrifuge tube vortexed to suspend the bacteria. In those tests involving "organic loads", a 1:1 dilution of the antimicrobial with whole milk was made before addition to the cultured microorganism to simulate conditions the product may have to experience in a real life environment, such as on a cow's teat.

The tube was then placed in a 37° C. water bath for 1 minute. The tube was centrifuged again at approximately 600 to 700 g for approximately five to ten minutes, and the supernatant decanted. The remaining precipitate was then suspended in a quencher solution containing letheen broth, 1% sodium thiosulfate and 0.2 mM $CaCl_2$. The tube was centrifuged at approximately 600 to 700 g for approximately five to ten minutes, decanted and washed a second time in the quencher solution.

The surviving bacteria suspended in quencher solution were then diluted with PBS and plated on appropriate media, for example, MacConkey for *Escherichia coli*, Staph 110 for *Staphylococcus*, and trypticase soy agar with 6% Sheep's blood for *Streptococcus*. The plates were incubated 24 to 48 hours at 37° C. and counted. The surviving organisms were expressed as colony forming units (CFU)/ml, and compared to the negative control as percent survival.

| STAPHYLOCOCCUS AUREUS | |
|---|---|
| Antimicrobial Tested | Percent Survival |
| undiluted antimicrobial | |
| 93% propylene glycol/7% water | 0.003 |
| 1% fatty acid mixture[a]/93% propylene glycol/6% water | 0 |
| 1% fatty acid mixture/70% propylene glycol/29% water | 0 |
| 0.5% iodophor | 0 |
| 1% iodophor | 0 |
| 0.5% chlorhexidine | 0 |
| Chlorine dioxide | 0 |
| diluted with organic load | |
| 93% propylene glycol/7% water | 30.83 |
| 70% propylene glycol/30% water | 94.23 |
| 0.25% fatty acid mixture/93% propylene glycol/6.75% water | 27.86 |
| 0.5% fatty acid mixture/93% propylene glycol/6.5% | 0 |
| 1% fatty acid mixture/99% propylene glycol | 0 |
| 1% fatty acid mixture/93% propylene glycol/6% water | 5.18 |
| 1% fatty acid mixture/70% propylene glycol/29% water | 3.65 |
| 1% fatty acid mixture/60% propylene glycol/39% water | 0 |
| 2% fatty acid mixture/93% propylene glycol/5% water | 0 |
| 3% fatty acid mixture/93% propylene glycol/4% water | 0 |
| 4% fatty acid mixture/93% propylene glycol/3% water | 0 |
| 5% fatty acid mixture/93% propylene glycol/2% water | 0 |
| 1% fatty acid mixture/70% propylene glycol/25% propanol/4% water | 0 |
| 1% fatty acid mixture[b]/70% propylene glycol/29% water | 3.36 |
| 0.5% iodophor | 0.70 |
| 1% iodophor | 0.003 |
| 0.5% chlorhexidine | 0.345 |
| chlorine dioxide | 16.96 |

[a] Unless otherwise indicated, all fatty acid mixtures are combinations of 55% $C_8$ and 40% $C_{10}$ aliphatic fatty acids by weight.
[b] This composition includes a mixture of 55% by weight of $C_{12}$ and 40% by weight of $C_{14}$ aliphatic fatty acids. The remaining 5% by weight is made up of other fatty acids of varying lengths.

| ESCHERICHIA COLI | |
|---|---|
| Antimicrobial tested | Percent Survival |
| undiluted antimicrobial | |
| 93% propylene glycol/7% water | 0 |
| 1% fatty acid mixture/93% propylene glycol/6% water | 0 |
| 1% fatty acid mixture/70% propylene glycol/29% water | 0 |
| 0.5% iodophor | 0 |
| 1% iodophor | 0 |
| 0.5% chlorhexidine | 0 |
| chlorine dioxide | 0 |
| diluted with organic load | |
| 93% propylene glycol/7% water | 2.43 |
| 0.25% fatty acid mixture/93% propylene glycol/6.75% water | 7.64 |
| 0.5% fatty acid mixture/93% propylene glycol/6.5% water | 0 |
| 1% fatty acid mixture/99% propylene glycol | 0 |
| 1% fatty acid mixture/93% propylene glycol/6% water | 0 |
| 1% fatty acid mixture/70% propylene glycol/29% water | 0 |
| 1% fatty acid mixture/60% propylene glycol/39% water | 0 |
| 2% fatty acid mixture/93% propylene | |

-continued

ESCHERICHIA COLI

| Antimicrobial tested | Percent Survival |
|---|---|
| glycol/5% water | |
| 3% fatty acid mixture/93% propylene glycol/4% water | 0 |
| 4% fatty acid mixture/93% propylene glycol/3% water | 0 |
| 5% fatty acid mixture/93% propylene glycol/2% water | 0 |
| 1% fatty acid mixture/70% propylene glycol/25% propanol/4% water | 0 |
| 1% fatty acid mixture[b]/70% propylene glycol/29% water | 0 |
| 0.5% iodophor | 0.003 |
| 1% iodophor | 0 |
| 0.5% chlorhexidine | 0 |
| chlorine dioxide | 0 |

[b]This composition includes a mixture of 55% by weight of $C_{12}$ and 40% by weight of $C_{14}$ aliphatic fatty acids. The remaining 5% by weight is made up of other fatty acids of varying lengths.

STREPTOCOCCUS AGALACTIAE
diluted with organic load

| Antimicrobial tested | Percent Survival |
|---|---|
| 1% fatty acid mixture/70% propylene glycol/29% water | 0 |
| 0.5% iodophor | 0 |
| 1% iodophor | 0 |
| 0.5% chlorhexidine | 0 |
| chlorine dioxide | 0 |

STREPTOCOCCUS UBERIS
diluted with organic load

| Antimicrobial tested | Percent Survival |
|---|---|
| 1% fatty acid mixture/70% propylene glycol/29% water | 0.08 |
| 0.5% iodophor | 0.01 |
| 1.0% iodophor | 0 |
| 0.5% chlorhexidine | 0.01 |
| chlorine dioxide | 5.19 |

STAPHYLOCOCCUS EPIDERMIDIS
diluted with organic load

| Antimicrobial tested | Percent Survival |
|---|---|
| 1% fatty acid mixture/70% propylene glycol/29% water | 0 |
| 0.5% iodophor | 0 |
| 1% iodophor | 0 |
| 0.5% iodophor | 0 |
| chlorine dioxide | 5 |

PSEUDOMONOAS AERUGINOSA
diluted with organic load

| Antimicrobial tested | Percent Survival |
|---|---|
| 1% fatty acid mixture/70% propylene glycol/29% water | 0 |
| 0.5% iodophor | 0 |
| 1% iodophor | 0 |
| 0.5% chlorhexidine | 28.98 |
| chlorine dioxide | 0 |

The results of in vitro tests performed in Example 1 indicate that an antimicrobial including varying concentrations of a mixture of fatty acids, propylene glycol and water are as efficacious as, if not more efficacious than, chemical compositions presently in use as teat dip antimicrobials. Additionally, these tests confirm that antimicrobials containing different mixtures of short to medium-chain fatty acids are as efficacious, if not more efficacious than, chemical compositions presently in use as teat dip antimicrobials.

EXAMPLE 2

Another set of in vitro tests were run on *Staphylococcus aureus, Escherichia coli*, and *Streptococcus uberis*. A culture of the microorganism was first prepared according to the following procedure. Six to ten milliliters of trypticase soy broth was inoculated with the organism under consideration from a frozen or refrigerated stock. After incubation for five to seven hours at 37° C., the culture was transferred to a flask containing 200 milliliters of trypticase soy broth. The culture in the flask was then incubated on a gyratory shaker at approximately 1500 rpm overnight at 37° C. The next day, the culture in the flask is washed once in PBS or 0.1% protease peptone, and stored at approximately 4° C. until required.

The tests were run using dairy cow teats which had been obtained from a slaughter house. The teats were cut off at their connection to the udder, cleaned, and all hair was removed by using an open flame. The teats selected for the testing were screened for lesions, cuts, scars or other abnormalities. The teats were stored until needed in plastic bags in ice at a temperature below freezing.

Immediately before the test, the teats were thawed in warm water and thoroughly dried with a paper towel. The thawed teats were suspended from clips attached to a horizontal rod. Prior to testing with the selected organism, the teats were disinfected by dipping the teat in a solution of 70% propanol and air-drying the teat.

The microorganism in question was placed in a 50 milliliter beaker for testing purposes. Each teat was dipped into culture and left to drain for five minutes. The teats were then dipped into a beaker containing the selected antimicrobial (or sterile water if control) and left to drain for ten minutes. Ten teats were tested per antimicrobial (or control).

The teats were then dipped into quencher solution to recover the surviving organisms. The quencher solution included Bacto-Letheen broth and 1% sodium thiosulfate.

The beakers containing the quencher solution and teat were suspended in an ultrasonic water bath and sonicated for 30 seconds. The solutions containing the surviving organisms were transferred to 25×150 millimeter tubes, vortexed, and diluted with PBS or 1% protease peptone.

Countable dilutions were plated on appropriate media, and incubated from 24 to 48 hours at 37° C. The colonies were counted macroscopically with the aid of fluorescent light.

Non-typical colonies were not counted. The results were expressed in CFU/ml, the log of the mean value of each antimicrobial was taken. The log values for the antimicrobials were then compared with the log value for the negative control to obtain a percent log reduction.

STAPHYLOCOCCUS AUREUS

| Antimicrobial tested | Percent Log Reduction |
|---|---|
| 1% fatty acid mixture/93% propylene glycol/6% water | 36.20 |
| 0.5% iodophor | 26.72 |
| 1% iodophor | 46.35 |
| chlorine dioxide | 33.90 |

ESCHERICHIA COLI

| Antimicrobial tested | Percent Log Reduction |
|---|---|
| 1% fatty acid mixture/93% propylene glycol/6% water | 37.80 |
| 0.5% iodophor | 32.38 |
| 1% iodophor | 45.17 |
| 0.5% chlorhexidine | 20.50 |
| chlorine dioxide | 22 |

STREPTOCOCCUS UBERIS

| Antimicrobial tested | Percent Log Reduction |
|---|---|
| 1% fatty acid mixture/93% propylene glycol/6% water | 29.5 |
| 1% iodophor | 22.47 |

The results of in vitro tests performed in Example 2 indicate that antimicrobials including fatty acids, propylene glycol and water are as efficacious as, if not more efficacious than, chemical compositions presently in use as teat dip antimicrobials.

EXAMPLE 3

A set of in vivo tests was run on *Staphylococcus aureus* and *Streptococcus agalactiae* using one hundred and fifty Holstein cows. The cows were housed in free stalls with concrete surfaces, bedded with dry shavings, and milked in a herringbone parlor.

The cows were screened for pre-existing infections of *Staphylococcus aureus*, *Streptococcus agalactiae*, and *Streptococcus uberis*, and for injuries on the teats. Cows experiencing other types of infections were divided equally among the test groups.

The control group was not treated with either a pre- or post-milking antimicrobial. A second group was treated with both a pre- and post-milking iodophor antimicrobial (0.5% iodophor). A third group was treated with another pre- and post-milking iodophor antimicrobial (1.0% iodophor). The remaining cows were treated before and/or after milking with a preferred embodiment of the present invention.

Where no pre-milking antimicrobial was used, the udder was forestripped, washed, and dried with a paper towel before milking. For animals receiving both pre- and post-milking antimicrobial applications, the udder was forestripped prior to a 20 to 30 second pre-milking application of antimicrobial, and then manually dried with a paper towel.

The milking machines were attached with three minutes after udder preparation, and removed by automatic detaching devices.

All teats were exposed to the microbe culture equally by dipping the teat in a suspension of the test microbe to a depth of approximately 25 mm immediately after the afternoon milking. After exposure to the culture, the teats were dipped immediately in the antimicrobial under consideration.

Duplicate milk samples from each quarter of udder of the test animals were collected and cultured weekly. Additional milk samples were collected from animals where the results from the first two samples differed. The results of the tests were expressed as a percent reduction.

STAPHYLOCOCCUS AUREAUS

| Antimicrobial tested | Percent Reduction |
|---|---|
| 1% fatty acid mixture/93% propylene glycol/6% water | 78.60 |
| 0.5% iodophor | 84.0 |
| 1% iodophor | 85.30 |

STREPTOCOCCUS AGALACTIAE

| Antimicrobial tested | Percent Reduction |
|---|---|
| 1% fatty acid mixture/93% propylene glycol/6% water | 60.30 |
| 0.5% iodophor | 77.30 |
| 1% iodophor | 79.20 |

The results of in vivo tests performed in Example 3 indicate that antimicrobials including fatty acids, propylene glycol and water are as efficacious as chemical compositions presently in use as teat dip antimicrobials.

EXAMPLE 4

In a further set of in vitro tests, the antimicrobial efficacy of an antimicrobial solution including a mixture of short to medium-chain fatty acids dissolved in propylene glycol was compared with an antimicrobial solution including a single length fatty acid dissolved in propylene glycol. The selected test culture was *Staphylococcus aureus*, and the procedure followed was that outlined above in Example 1.

| diluted with organic load | |
|---|---|
| Antimicrobial tested | CFU/ml |
| Control | $6.5 \times 10^8$ |
| 1% fatty acid mixture/99% propylene glycol | 70 |

-continued

| diluted with organic load | |
|---|---|
| Antimicrobial tested | CFU/ml |
| 1% $C_{10}$ fatty acid/99% propylene glycol | $4.03 \times 10^3$ |

The test performed in Example 4 confirm that a significant difference in antimicrobial effect occurs when a mixture of short to medium-chain fatty acids are used in comparison with the use of a single length fatty acid.

In part, the impressive antimicrobial effect of the present invention is thought to be caused by the mixture of short to medium-chain fatty acids. In fact, it has been theorized that the longer chain molecules ($C_{10}$ to $C_{12}$), such as are used in the compositions disclosed herein, have a significant efficacy against certain bacteria, especially gram positives.

Additionally, propylene glycol also has a measurable antimicrobial effect, as can be seen in the results presented in Example 1, and as recognized by others in the art. It has been suggested that certain species, and strains within species of bacteria, are particularly susceptible to the bactericidal effects of propylene glycol. See P. A. Thomas et al., Antibacterial Properties of Dilute Formocresol and Eugenol and Propylene Glycol, Oral Surgery, February 1980 and I. Olitzky, Antimicrobial Properties of a Propylene Glycol Based Topical Therapeutic Agent, Journal of Pharmaceutical Sciences, May 1965.

However, the results also show an increased antimicrobial response when the fatty acids are combined with propylene glycol, or others of the solvents listed above. Although not intending to be bound by any theory, it is believed, that the degree of increased bactericidal efficacy of the fatty acids is determined to a large degree by the polarity of the solvent. It is further believed that the polarity of propylene glycol, or others of the solvents listed above, is uniquely suited to trigger a synergistic reaction between the solvent and the solute.

Polarity or conductivity of a material is a measurement of the dielectric constant, the ratio of electric displacement to electric field intensity. At one extreme, is a vehicle such as water, with a very high polarity, and dielectric constant of 88. At the other extreme, petroleum and vegetables oils (such as olive or cottonseed oil) have a very low polarity, with a dielectric constant of about 2. Propylene glycol is moderately polar, with a dielectric constant of about 32. By comparison, low molecular weight alcohols have lower polarities, with dielectric constants in the range of 15 to 25.

It is believed that a greater degree of antimicrobial efficacy occurs when the fatty acids are solubilized in lipophilic high polarity solvents versus when they are solubilized in lipophilic low polarity solvents. When 1% by weight of a mixture of 55% $C_8$ and 40% $C_{10}$ fatty acids is added to lipophilic, high polarity solvents such as propylene glycol, glycerol, ethylene glycol or isopropanol, the bactericidal efficacy against such organisms as *Staphylococcus aureus* and *Escherichia coli* is impressive. However, when the same concentration of fatty acids is solubilized in such low polarity lipophilic solvents such as corn oil or mineral oil, the bactericidal efficacy of the fatty acid component decreases significantly, with a large number of the organisms surviving the treatment.

EXAMPLE 5

In a further set of in vitro tests, the antimicrobial efficacy of a fatty acid antimicrobial in solvents of various polarities was tested. The selected test cultures were *Staphylococcus aureus* and *Escherichia coli*, and the procedure followed was that outlined above in Example 1.

| *STAPHYLOCOCCUS AUREUS* diluted with organic load | | |
|---|---|---|
| Vehicle | Dielectric constant | Percent Survival |
| Corn oil | 2-4 | 41.5 |
| Mineral oil | 2-4 | 100 |
| Propylene Glycol | 41 | 5.2[a] |
| Ethylene Glycol | 41 | 0.5[a] |
| Glycerol | 47 | 14.86[a] |
| Water[b] | 88 | 0 |

[a] Propylene glycol, ethylene glycol, and glycerol have a minimal amount of antimicrobial efficacy in this system.
[b] Fatty acids are, at best, only slightly soluble in water. The fatty acids in this composition are solubilized by adding an anionic hydrotrope and lowering the pH below 4.0.

| *ESCHERICHIA COLI* diluted with organic load | | |
|---|---|---|
| Vehicle | Dielectric Constant | Percent Survival |
| Corn oil | 2-4 | 56.18 |
| Mineral oil | 2-4 | 6.86 |
| Propylene Glycol | 41 | 0[a] |
| Ethylene Glycol | 41 | 0[a] |
| Glycerol | 47 | 0[a] |
| Water[b] | 88 | 0 |

[a] Propylene glycol, ethylene glycol, and glycerol have a minimal amount of antimicrobial efficacy in this system.
[b] Fatty acids are, at best, only slightly soluble in water. The fatty acids in this composition are solubilized by adding an anionic hydrotrope and lowering the pH below 4.0.

The results of the in vitro tests performed in Example 5 indicate that an antimicrobial solution of fatty acids in solution with propylene glycol, ethylene glycol or glycerol, or solubilized in water, are effective antimicrobials, whereas solutions using corn oil and mineral oil are generally less effective antimicrobials.

The exact theory behind the synergistic reaction between the mixtures of fatty acids and the lipophilic polar solvents is as of yet unknown. However, Corner reported a similar synergistic response when $C_8$ fatty acids were added to fatty alcohols such as octanol. Corner concluded that the fatty acids interact with lipophilic companion molecules, such as alcohols, so as to shield the charges on the polar end of the fatty acid molecule. The shielding is thought to protect the proton shuttle mechanism that is responsible for uncoupling the transmembrane proton gradients in the membrane of bacterial cells which, in turn, inhibits that cells' ability to grow. Corner also hypothesized that the fatty acids helped disperse alcohol micelle aggregates which allowed the alcohol to have better contact with cells, thereby increasing its ability to kill more cells.

It cannot be concluded, however, based on the tests run to date, whether the propylene glycol is indeed aiding the fatty acids as theorized by Corner above, or if the acids are aiding the propylene glycol in some yet unknown fashion, or if there is a mutual synergism occurring. Empirical data is not available in the laboratory or in the literature that would fully explain the synergism observed.

Testing has confirmed that the preferred embodiments of the present invention are non-irritating to the skin. This characteristic of the present invention has been demonstrated in vivo using the standard dermal irritation test with rabbits, commonly referred to as the Draize skin test. These results were confirmed using high sensitivity dermal response in vitro technology, namely the two-part system (including an artificial membrane-dye and a macromolecular matrix) manufactured by In-Vitro International and sold as the "IRRITECTION" Assay System or the "SKINTEX" Assay System.

In fact, it is believed that the high percentage of glycol in the preferred embodiments enhances this invention's non-irritating characteristics, and may actually help protect and heal the skin. Glycols, such as propylene glycol, are widely known as humectants with very good skin protecting properties.

It should also be noted that the components of this product are also non-toxic. The fatty acids (at the low concentrations proposed) and propylene glycol are both considered safe, with propylene glycol being recognized as a good grade material by the Food and Drug Administration. There is no evidence that the concentrations of fatty acids or propylene glycol present in the scope of the present invention are harmful to animals, humans or the environment.

Additionally, the preferred embodiments of the present invention have superior residual activity to those chemical germicides presently being used as teat dips, washes, sprays and wipes. Given the solubility of fatty acids in propylene glycol, the concentrations of fatty acids and propylene glycol are known to be stable over time even with variations in such conditions as temperature, humidity, and contamination with milk. Moreover, because of the high percentage of propylene glycol, this product has a relatively high viscosity, being considerably higher than that of water and many other products utilized today in the dairy industry as post-milking teat dips. The higher viscosity gives this product the ability to stay on the teat longer at a higher concentration.

Still other aspects, objects and advantages of the present invention can be obtained from a study of the specification and the appended claims.

The invention claimed is:

1. A method for reducing the incidence of mastitis in a dairy animal, the method comprising the step of:
    topically applying an antimicrobial composition to the teats of the animal,
    the composition consisting essentially of:
    (1) from about 60% to about 95% of a lipophilic polar solvent selected from the group consisting of: propylene glycol, ethylene glycol, glycerol, isopropanol, and combinations thereof, by weight of the composition; and
    (2) at least two $C_8$ to $C_{14}$ fatty acids in a total amount of from about 0.5% to about 5% by weight of the composition.

2. The method of claim 1, where the lipophilic polar solvent is propylene glycol.

3. The method of claim 1, where the lipophilic polar solvent is present in an amount from about 60% to about 75% by weight of the composition.

4. The method of claim 1, wherein the fatty acids form a fatty acid mixture which comprises about 55% by weight of the fatty acid mixture of a $C_8$ fatty acid and about 40% by weight of the fatty acid mixture of a $C_{10}$ fatty acid.

5. The method of claim 1, wherein the lipophilic polar solvent has a dielectric constant of greater than about 18.

6. The method of claim 1, and comprising:
    from about 0.5% to about 39.5% of a secondary solvent, by weight of the composition.

7. A method for reducing the incidence of mastitis in a dairy animal, the method comprising the step of:
    topically applying an antimicrobial composition to the teats of the animal,
    the composition consisting essentially of:
    (1) from about 60% to about 95% of a lipophilic polar solvent selected from the group consisting of: propylene glycol, ethylene glycol, glycerol, isopropanol, and combinations thereof, by weight of the composition;
    (2) up to about 39.5% of a secondary solvent, by weight of the composition; and
    (3) at least two $C_8$ to $C_{14}$ fatty acids in a total amount of from about 0.5% to about 5% by weight of the composition, wherein the antimicrobial composition has a pH below about 4.

8. The method of claim 1, wherein one of the fatty acids is caprylic acid.

9. The method of claim 1, wherein one of the fatty acids is capric acid.

10. A method for reducing the incidence of mastitis in a dairy animal, the method comprising the step of:
    topically applying an antimicrobial composition to the teats of the animal,
    the composition consisting essentially of:
    from about 60% by weight of the composition to about 95% by weight of the composition of a lipophilic polar solvent having a dielectric constant greater than about 18, and at least two $C_8$ to $C_{14}$ fatty acids in the total amount of from about 0.5% to about 5% by weight of the composition.

11. The method of claim 10, wherein the lipophilic polar solvent is selected from a group consisting of propylene glycol, ethylene glycol, glycerol, isopropanol, and combinations thereof.

12. The method of claim 10, wherein the fatty acids form a fatty acid mixture which comprises about 55% by weight of the fatty acid mixture of a $C_8$ fatty acid and about 40% by weight of the fatty acid mixture of a $C_{10}$ fatty acid.

13. A method for reducing the incidence of mastitis in a dairy animal, the method comprising the step of:
    topically applying an antimicrobial composition to the teats of the animal,
    the composition consisting essentially of:
    from about 60% by weight of the composition to about 95% by weight of the composition of a lipophilic polar solvent having a dielectric constant greater than about 18; up to about 39.5% of a secondary solvent by weight of the composition; and at least two $C_8$ to $C_{14}$ fatty acids in the total amount of from about 0.5% to about 5% by weight of the composition;
    wherein the antimicrobial composition has a pH below about 4.

14. The method of claim 10, wherein at least one of the fatty acids in the antimicrobial composition is selected from a group consisting of:
    a $C_{12}$ fatty acid and a $C_{14}$ fatty acid.

15. The method of claim 10, wherein at least one of the fatty acids in the antimicrobial composition is a $C_8$ fatty acid.

16. A method for reducing the incidence of mastitis in a dairy animal, the method comprising the step of:
    topically applying an antimicrobial composition to the teats or udder of the animal, the composition consisting essentially of:
    from about 60% to about 95% of a lipophilic polar solvent having a dielectric constant greater than about 18 by weight of composition;
    at least two $C_8$ to $C_{14}$ fatty acids in a total amount from about 0.5% to 5% by weight of the composition; and from about 0.5% to about 39.5% of a secondary solvent, by weight of composition.

17. The method of claim 16, wherein the lipophilic polar solvent is selected from the group consisting of propylene glycol, ethylene glycol, glycerol, and combinations thereof.

18. The method of claim 16 wherein the lipophilic polar solvent is present in the amount from about 50% to about 75% by weight of composition.

19. The method of claim 16 wherein one of the fatty acids is caprylic acid.

20. The method of claim 16 wherein one of the fatty acids is capric acid.

21. An antimicrobial composition for reducing the incidence of mastitis in a dairy animal, the composition consisting essentially of:

(1) from about 60% to about 95% of a lipophilic polar solvent selected from the group consisting of propylene glycol, ethylene glycol, glycerol, isopropanol, and combinations thereof, by weight of the composition; and (2) at least two $C_8$ to $C_{14}$ fatty acids in a total amount of from about 0.5% to about 5% by weight of the composition; and (3) from about 0.5% to about 39.5% of a secondary solvent, by weight of composition.

22. The antimicrobial composition of claim 21, wherein the antimicrobial composition has a pH below about 4.

23. The antimicrobial composition of claim 21, wherein the fatty acids are selected from the group consisting essentially of: $C_8$, $C_9$, $C_{10}$, $C_{12}$, and $C_{14}$, fatty acids.

24. The method of claim 21, wherein the lipophilic polar solvent has a dielectric constant of greater than about 18.

* * * * *